United States Patent [19]

Schenk et al.

[11] Patent Number: 5,895,389

[45] Date of Patent: Apr. 20, 1999

[54] DRILLING GUIDE AND MEASURING INSTRUMENTATION

[75] Inventors: Beat Simon Schenk, Paoli, Pa.; James M. Green, Portland, Oreg.

[73] Assignee: Synthes (U.S.A.), Paoli, Pa.

[21] Appl. No.: 08/865,266

[22] Filed: May 29, 1997

[51] Int. Cl.$^6$ ............................................. A61B 17/17
[52] U.S. Cl. ............................ 606/96; 606/102; 606/80
[58] Field of Search .......................... 606/80, 86, 87, 606/96, 97, 98, 102, 104

[56] References Cited

U.S. PATENT DOCUMENTS

| | | |
|---|---|---|
| 1,327,114 | 6/1920 | Rhein . |
| 1,831,813 | 11/1931 | Levedahl . |
| 2,235,419 | 3/1941 | Callahan et al. . |
| 2,267,157 | 12/1941 | Lippincott . |
| 2,427,128 | 9/1947 | Ettinger . |
| 2,494,229 | 1/1950 | Collison . |
| 3,530,860 | 9/1970 | Majoros . |
| 3,752,161 | 8/1973 | Bent . |
| 3,835,860 | 9/1974 | Garretson . |
| 3,892,232 | 7/1975 | Neufeld . |
| 3,897,786 | 8/1975 | Garnett et al. . |
| 3,913,584 | 10/1975 | Walchle et al. . |
| 4,005,527 | 2/1977 | Wilson et al. . |
| 4,233,979 | 11/1980 | Naser . |
| 4,341,206 | 7/1982 | Perrett et al. . |
| 4,409,973 | 10/1983 | Neufeld . |
| 4,450,834 | 5/1984 | Fischer . |
| 4,549,538 | 10/1985 | Schadrack, III et al. . |
| 4,574,794 | 3/1986 | Cooke et al. . |
| 4,586,497 | 5/1986 | Dapra et al. . |
| 4,708,139 | 11/1987 | Dunbar, IV . |
| 4,710,075 | 12/1987 | Davidson ............................ 408/202 |
| 4,739,751 | 4/1988 | Sapega et al. . |
| 4,813,407 | 3/1989 | Vogen . |
| 4,838,742 | 6/1989 | Fricker ................................. 409/131 |
| 4,883,048 | 11/1989 | Purnell et al. . |
| 4,978,351 | 12/1990 | Rozas ................................... 606/98 |
| 5,013,318 | 5/1991 | Spranza, III ......................... 606/102 |
| 5,026,375 | 6/1991 | Linovitz et al. ..................... 606/79 |
| 5,026,376 | 6/1991 | Greenberg ........................... 606/96 |
| 5,112,337 | 5/1992 | Paulos et al. ....................... 606/96 |
| 5,122,146 | 6/1992 | Chapman et al. .................. 606/102 |
| 5,133,720 | 7/1992 | Greenberg ........................... 606/96 |
| 5,180,388 | 1/1993 | DiCarlo .............................. 623/16 |
| 5,197,967 | 3/1993 | Wilson .............................. 606/79 |
| 5,207,753 | 5/1993 | Badrinath ............................ 606/96 |
| 5,409,490 | 4/1995 | Ethridge ............................ 606/80 |
| 5,409,493 | 4/1995 | Greenberg ........................... 606/96 |

FOREIGN PATENT DOCUMENTS

| | | |
|---|---|---|
| 645252 | 7/1962 | Canada . |
| 2 598 311 | 11/1987 | France . |

*Primary Examiner*—Michael Buiz
*Assistant Examiner*—David O. Reip
*Attorney, Agent, or Firm*—Pennie & Edmonds LLP

[57] ABSTRACT

A surgical drilling guide for guiding a drilling tool, measuring its penetration depth, and protecting surrounding tissue. The guide has a sleeve and a plunger that telescopes within the sleeve. The plunger and the sleeve have axial bores adapted to slidably receive a portion of the tool that protrudes beyond a drill chuck. The extended length of the drilling guide is substantially as long as the length of the protruding portion of the tool, and a maximum extended length of the guide is preferably as long as the protruding portion. As the tool in drilled into a workpiece, the chuck collapses the drilling guide. Gradations on the side of the guide indicate workpiece-penetration depth.

24 Claims, 2 Drawing Sheets

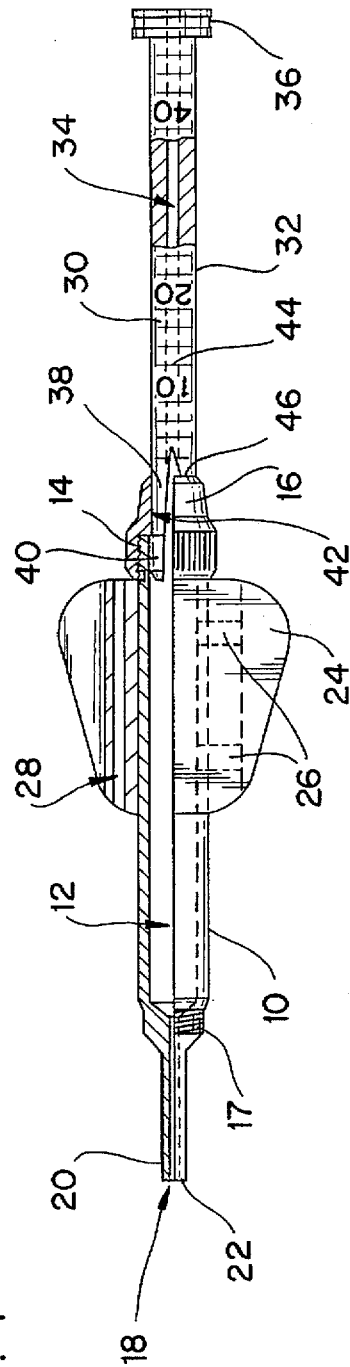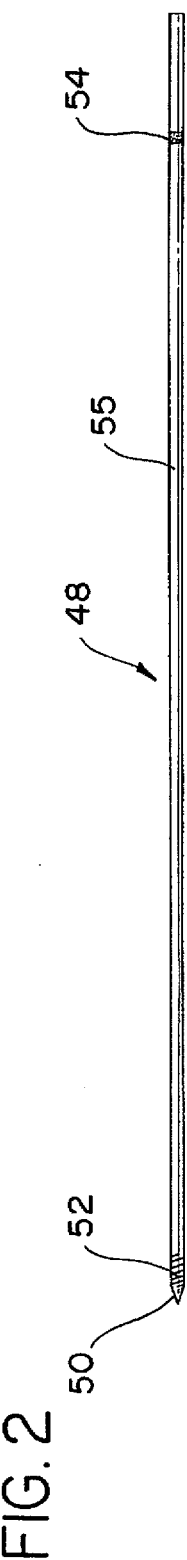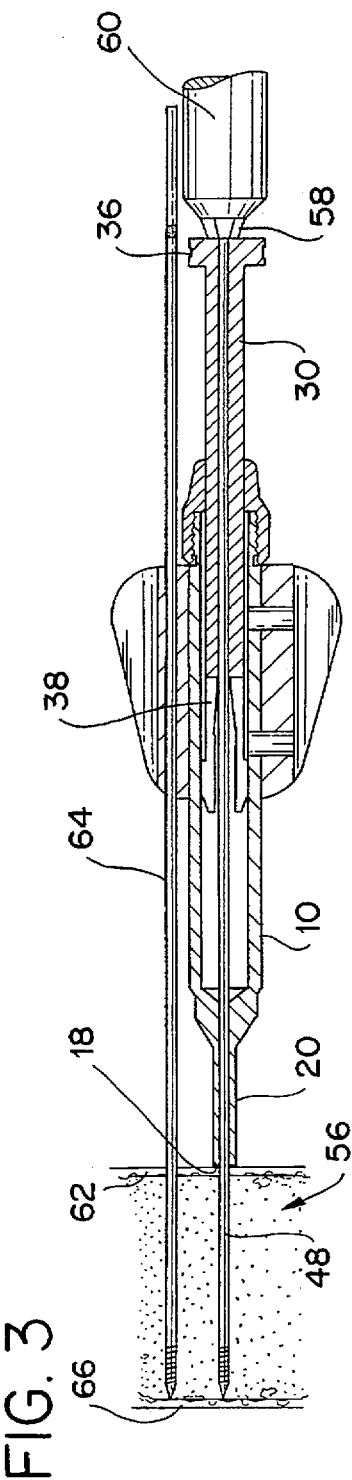

DRILLING GUIDE AND MEASURING INSTRUMENTATION

FIELD OF THE INVENTION

The invention relates to instrumentation for guiding a drilling tool and measuring its depth of penetration into a workpiece. More particularly, the invention relates to a surgical drilling-guide for concurrently guiding a drilling tool, measuring its implantation depth, and protecting surrounding tissue.

BACKGROUND OF THE INVENTION

Numerous ostoesynthetic procedures reduce fractures through the implantation of fasteners for fixing bone fragments. Many of these procedures require a determination of the length of a bore to be drilled or of a fasteners to be implanted in a bone. Proper bone penetration or implantation depths of fasteners are crucial, especially in small bones, small bone fragments, and in intra-articular regions where excessive penetration can damage surrounding tissues, including intra-articular cartilage.

In many modern procedures, a surgeon implants a guide wire into a bone to guide subsequent tools and fasteners, such as cannulated drills, screws, and nails. The surgeon must ensure that the guide wire penetrates the bone to a desired depth, in many cases up to, but not beyond, the distal bone cortex. Guide wire insertion is commonly performed while monitoring the guide wire's trajectory in relation to the bone with a mobile fluoroscopy unit. Kirschner wires or pins are also employed in certain procedures. Kirschner wires are similar to guide wires, but are generally thinner and have no threads.

Once the guide wire is in place, the surgeon must then determine the actual depth of guide wire implantation. Known instruments require surgeons to perform an additional step and use additional instruments after drilling in the guide wire to make this determination.

A common instrument used for measuring guide-wire implantation is described in U.S. Pat. No. 4,341,206. The instrument is a tube with a C-shaped cross-section so that its interior channel is visible along a longitudinal slit. A scale is marked on the outside of the tube, adjacent the slit. After implanting the guide wire, the surgeon must detach the drill from the guide wire and slide the tube over the exposed end of the wire until it contacts the surface of the bone. The unimplanted tip of the guide wire is thus visible through the slit. The scale on the tube is calibrated to provide a numerical reading of the penetration depth of the particular length of wire used. This numerical value is obtained by reading off the number on the scale aligned with the unimplanted guide-wire tip.

U.S. Pat. No. 5,122,146 discloses another instrument designed to measure the depth of guide wire insertion into a medullary canal of a femur. The instrument comprises a graduated hollow shaft designed to receive and secure a guide wire within the shaft. A sleeve slides along the outside of the shaft and carries a pointer that lines up with the graduations to indicate depth. According to the patent's teaching, a surgeon initially drills a guide pin into the medullary canal, then enlarges the entry hole with a hipbolt reamer, and subsequently removes both the pin and the reamer. The surgeon then inserts a bead-tipped guide wire into the instrument and then through the reamed entry hole. The surgeon slides the instrument until a part of it is flush with the proximal portion of the guide wire and locks them together. At this point, a portion of the instrument's shaft is disposed within the bone. To measure the depth of the hole and of the subsequent implant needed, the sleeve is slid down the instrument until it abuts a proper portion of the bone, which in the described case is the tip of the greater trochanter. The sleeve may be locked in place and the depth read either before or after the instrument is removed from the bone.

Several other patents teach gauges that are themselves inserted into the bone to determine the depth of a drilled hole when a guide wire is not used. U.S. Pat. No. 5,013,318 shows a depth gauge with a sliding disk on an indexed shaft. The gauge is inserted into a hole in the bone that is smaller than the disk. When the shaft is fully inserted, the surgeon may either read the last marking remaining on the outside of the bone, or may slide the disk against the bone and read the depth after removing of the gauge from the bone.

Another bone-penetration depth gauge appears in U.S. Pat. No. 4,450,834. This gauge comprises a probe that telescopes within a handle. An indicator tab is fixed to the probe and slides within a longitudinal slit made through the side of the handle, adjacent a graduated scale. The physician slides probe within the handle by sliding the tab and may thus take measurements by reading the positions of the tab against the scale.

Other known instruments guide a drill bit or a pin during implantation. Some also prevent the drilling tool from penetrating any deeper than a preset value, but these instruments demand a prior determination of the necessary preset value by procedures such as those discussed above.

U.S. Pat. No. 4,549,538, for example, teaches a pin-inserter sheath adapted to attach to a drill. A drilling guide with multiple telescoping segments retracts against a surface of the drilled tissue as the pin penetrates the tissue. No graduations are provided.

U.S. Pat. No. 5,409,493 discloses a drill guide that can be telescopically collapsed to a desired length for limiting bone penetration. A scale on an inner telescoping tube may be used to indicate the amount by which the guide has been collapsed. After determination of the required drilling depth with another instrument, the surgeon partially collapses the instrument by squeezing a handle until the length of the instrument equals the length of the drill bit less the desired drilling depth. The surgeon then begins the drilling operation through the guide until he or she reaches the selected depth.

As mentioned above, the prior art instruments for determining drill penetration or guide-wire implantation depth require surgeons to perform an additional step and operate different apparatuses. These techniques require removing the drill and either inserting a gauge in the remaining open hole, or placing a measuring device over the external portion of the guide wire. Moreover, gauges that must be inserted into an open hole are not compatible with procedures that call for drilling, nailing, or screwing cannulated instruments axially along a preimplanted guide wire, as the gauges would require the guide wire to be extracted before measurement.

The high hourly cost of operating rooms today presents a serious drawback to procedures requiring time-consuming multiple steps. Some surgeons are tempted to avoid spending time using precise measuring instruments, and instead hold a ruler up to the unimplanted portion of the guide wire or compare this portion with a second guide wire of the same length to get an approximate depth determination. Moreover, if surgeons also omit the use of a drilling guide, tissue surrounding the drilling tool can be harmed, and thin tools such as guide wires can bow, altering their insertion angle.

3

None of the prior art instruments provide an instantaneous, continuous, and direct reading of the drilling depth of a guide wire or other drilling tool. Known devices do not permit a surgeon, in a single step, to implant a guide wire and determine the length of a subsequent tool or fastener to be implanted over the guide wire. Moreover, previous instruments do not simultaneously protect surrounding tissue from a spinning drill bit or guide wire, support the guide wire, and provide an instantaneous depth indication without the need to make calibrations or calculations to account for the length of the tool protruding from a drill chuck.

SUMMARY OF THE INVENTION

The present invention provides both a collapsible drilling-guide for instantaneously and continuously determining drilled depth and a method of determining this drilled depth. The invention is described in embodiments for orthopedic surgery, in which case the workpiece drilled into is a bone. The invention, however, is also applicable with other types of workpieces.

The drill guide has a workpiece-abutment member and a chuck-abutment member, each of which is collapsible with respect to the other. In the preferred embodiment, the chuck-abutment member is a plunger that slides telescopically within the workpiece-abutment member, which is a sleeve. The plunger and one end of the sleeve have axial bores sized to receive and guide a drilling tool.

A plurality of fingers on the forward end of the plunger are biased inwardly by an inside wall of the sleeve, providing a frictional, sliding fit. Each finger has a head on its tip. Together, the heads form a diameter slightly greater than that of the main body of the plunger. These heads act as stops to prevent the plunger from retracting out from the sleeve when the heads contact an endcap that is fixed to the rear end of the sleeve and that has approximately the diameter of the plunger's main body.

A platform at the rear end of the plunger provides a surface for a drill chuck to press against to collapse the telescoping drilling-guide. Preferably, the drilling guide extends to the length of the drilling tool to be used. A graduated scale on the outside of the plunger indicates the depth to which the drilling tool has penetrated the bone.

The sleeve of the preferred embodiment has a handle for controlling the drilling guide. An alignment bore preferably extends through the handle in parallel with the axis of the sleeve and plunger bores. By sliding the alignment bore over a preinserted guide wire, the drilling guide may be aligned with the parallel wire at a predetermined distance therefrom.

The invention also provides a drilling tool with indicia placed at a certain point along its length for a surgeon to align with a part of the drill, such as the front of the chuck, to assure that the portion of the tool protruding from the chuck will be as long as the extended drilling-guide. Thus, the scale will directly indicate the tool's depth.

In alternative embodiments, the plunger, sleeve, and endcap have noncircular cross-sections to prevent rotation between the sleeve and the plunger.

As a result, the invention provides a current depth indication while simultaneously protecting surrounding tissue and guiding a drilling tool. No sequential steps are necessary during surgery to provide these functions.

BRIEF DESCRIPTION OF THE DRAWINGS

FIG. 1 shows a side view of a partial cross-section of a measuring drill guide according to the present invention.

FIG. 2 illustrates a drilling tool according to the invention.

FIG. 3 shows a cross-section of the embodiment of FIGS. 1 and 2 being used to drill a threaded guide wire into a bone.

DETAILED DESCRIPTION OF THE PREFERRED EMBODIMENTS

Figure 4:
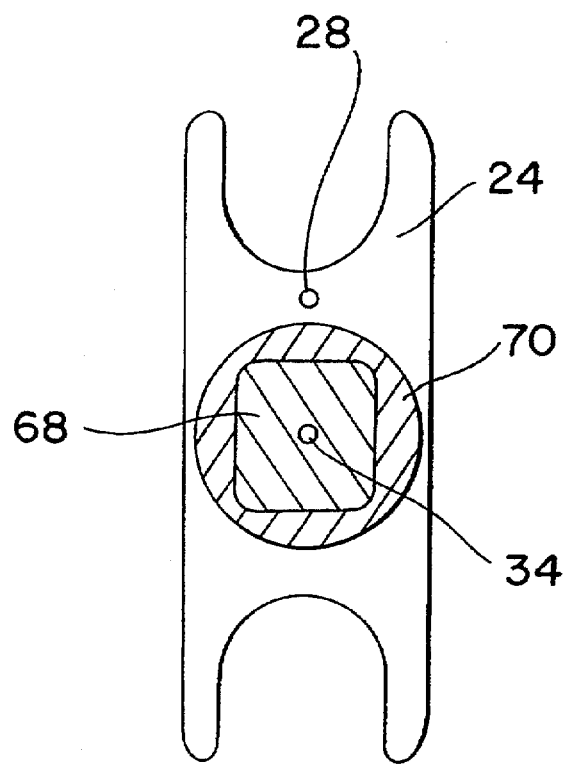
FIG. 4 is a forward-looking cross-sectional view through the endcap of another embodiment of the invention.

FIG. 1 shows a drilling tool guide according to the present invention for use with a guide wire. The guide has a hollow sleeve 10 with a bore 12 of preferably cylindrical cross-section. The rear end 14 of the sleeve 10 is preferably threaded on its outer surface to screw to a hollow endcap 16. Preferably, another portion 17 of the outer surface of sleeve 10 is threaded to screw to a separate drill guide (not shown).

A bore 18 extends through the front tip 20 of the sleeve 10. Preferably, the tip bore 18 is sized to guide a drilling tool, such as a threaded guide wire or a Kirschner wire, but may have a diameter appropriate to other tools such as drill bits or fixation pins. The outer diameter of tip 20 is preferably as narrow as practical to seat closely around a drilling site, but still maintain the structural integrity needed to guide a spinning tool. Also, serrations 22 preferably line the front side of the tip 20 to frictionally grip a bone surface during drilling to prevent the drilling guide from sliding on the bone's slippery periosteum, a fibrous membrane that covers the surface of the bone.

The preferred embodiment is handheld. It has a handle 24 secured to sleeve 10 by two pins 26. In this embodiment, the pins 26 penetrate the wall of the sleeve 10, but do not extend beyond the interior surface of the wall of sleeve 10. The handle 24 also has an alignment bore 28. The alignment bore 28 is sized to receive a parallel guide-wire that has already been inserted into a bone. Preferably, the alignment bore 28 extends in parallel to the intended drilling axis at a predetermined distance therefrom.

A plunger 30 slides telescopically within the sleeve 10. The main body 32 of the plunger 30 is preferably narrower than the sleeve bore 12.

A plunger bore 34 extends axially through the length of the plunger 30 and is shaped to receive and guide a spinning tool. This bore is axially aligned with the tip bore 18 of sleeve 10 in order to guide the tool along a straight line into the bone. Moreover, the plunger 30 and the sleeve 10 together protect tissue surrounding the drilling site.

The rear of the plunger 30 terminates in a platform 36. Platform 36 is adapted to abut the front of a spinning drill chuck, so that the chuck can force the plunger 30 forward and deeper into the sleeve 10. The platform 36 also provides a surface that a user can grasp to pull the plunger 30 backwards, extending the drilling guide.

The forward end of the plunger 30 is divided into a plurality of resilient fingers 38. In the preferred embodiment, finger heads 40 on the fingers 38 naturally form a slightly larger diameter than that of the sleeve bore 12. Most preferably, the fingers are tapered to produce a constant deflection along their lengths when a force is applied to their tips, producing fairly uniform bending moments throughout each finger. Thus, when the fingers 38 are inserted within the sleeve bore 12, the inner wall of the sleeve 10 biases the fingers 38 inwardly. This fit permits the plunger 30 to telescope within the sleeve 10 under friction, so the plunger 30 and the sleeve 10 retain their relative telescopic position after they have been partially collapsed.

As explained above, a front end of the hollow endcap 16 is screwed to the rear 14 of the sleeve 10. A rear endcap bore 42, behind the threaded portion, has an inner diameter that approximately matches the outer cross-section of the main body 32 of the plunger 30. When the endcap 16 is screwed onto the rear 14 of the sleeve 10, it prevents the finger heads 40 from retreating backwards beyond the endcap bore 42. Thus, the telescoping sleeve 10 and plunger 30 of this embodiment may only extend up to a predetermined maximum, as shown in FIG. 1. This maximum extension should be at least as long as the portion of a drilling tool that protrudes from a chuck, and preferably at most as long as that portion of the tool.

A scale 44 graduates the outside of the plunger 30 and indicates the amount by which the guide has been collapsed. FIG. 1 shows numerical markings at every 10 units, and graduations 44 at every 2 units. The graduations 44 in this embodiment are read against the rear end 46 of the endcap 16, although other embodiments can employ alternative forms of scale indicators. In the illustrated, maximally extended position, the scale 44 reads zero. As the plunger 30 is introduced further into the sleeve 10, the endcap rear end 46 indicates a higher number.

FIG. 2 shows a drilling tool 48, in this case a self tapping, surgical guide-wire according to the invention. The front tip 50 of the guide wire 48 preferably has sharp facets and ends at an acute point for cutting through bone. In the illustrated embodiment, the guide wire 48 has self-tapping threads 52, but other embodiments, such as Kirschner wires, pins, and drill bits, may not exhibit this feature.

To facilitate the use of the guide wire 48, indicia 54 marks the portion of the guide wire 48 to be inserted into the chuck of a drill. The distance from this indicia 54 to the tip 50 of the wire 48 preferably equals the fully extended length of the guide. Thus, if a surgeon properly loads the wire 48 into a chuck and aligns the front of the chuck with the indicia 54, the portion 55 of the wire protruding from the drill will be as long as the extended drilling-guide. If the surgeon places serrated tip 30 against a bone, as the surgeon drills the tool 48 into a bone through the drilling guide, the scale 44 indicates the length of the portion of the tool 48 that extends beyond the tip 20 of the sleeve 10, the frontmost part of the guide, and thus the scale 44 indicates the length of the wire 48 presently drilled into the bone. If an intermediate object is placed between the tip 30 and the bone, the penetration depth indicated includes the part of the intermediate object through which the wire 48 is currently passed.

FIG. 3 shows the guide wire 48 of FIG. 2 being implanted into a bone 56. After having closed a drill chuck 58 of drill 60 around the wire 48 so that the tip of the chuck 48 aligns with indicia 54, the surgeon has slid guide wire 48 into the guide. In the figure, the serrations 18 at the front tip 20 of the sleeve 10 rest against the proximal bone-cortex 62 or its periosteum.

In the illustrated use, guide wire 48 is being implanted at a predetermined distance from, and parallel to, a parallel guide-wire 64 that has already been implanted. The alignment bore 28 has been slid over the parallel wire 64 as shown.

As the surgeon operates the drill 60, the chuck 58 pushes the platform 36 and the plunger 30 forward, gradually collapsing the guide. The surgeon may monitor the progress of the wire 48 with lateral x-ray imaging. At any point during the insertion of the wire 48, the current depth of the wire is indicated on the scale 44. The surgeon stops drilling when the tip 50 of wire 48 reaches the appropriate depth within the bone 56. This is usually when the wire 48 reaches the distal bone-cortex 66, which is visible under lateral imaging.

The surgeon may read the indicated depth at this point. Otherwise, the surgeon may read the depth after detaching the drill 60 and removing the drilling guide, provided that a mechanism retains the sleeve 10 and the plunger 30 in relative stasis, as does the frictional association between the plunger fingers 38 and the inner wall of sleeve 10.

As a result of its construction, during insertion, the drilling guide provides simultaneous support for the guide wire 48, implantation depth indication, and protection of surrounding tissue.

Certain procedures require a surgeon to use a separate, specialized drill-guide. One percutaneous procedure necessitates screwing a bullet nosed insert, called a trocar, into a drill guide, piercing the patients skin with the trocar far enough so the trocar touches bone, and unscrewing the trocar prior to drilling when the separate drill-guide is firmly seated against the skin. In an embodiment of the invention adapted for this procedure, the threaded portion 17 of the sleeve 10 is sized to screw into the separate drill guide from where the trocar was removed.

In the preferred embodiment, the sleeve 10, the plunger 30, and the endcap 16 have round cross-sections. FIG. 4 shows an alternative embodiment with a plunger 68 of noncircular cross-section. The square cross-section in the figure is seen from a forwardly facing view taken through endcap 70. In this embodiment, the inner cross-section of the sleeve, hidden from view behind the endcap 70, preferably also matches the noncircular shape of the plunger 68. Embodiments with noncircular cross-sections prevent relative rotation between the plunger 68 and the sleeve 10.

Because the plunger 68 is not round, the endcap 70 is preferably fixed to the sleeve in a manner different from screwing a threaded endcap onto a threaded sleeve, as is preferred in embodiments of circular cross-section. The endcap 70 can be secured to the sleeve by bonding or with other fasteners, for instance.

Other noncircular embodiments, for example, have a key fixed to the sleeve or the plunger and slidably engaging a slot in the other of the two. This key in slot arrangement also limits rotation while permitting telescopic movement of the drilling guide.

Figure 5:
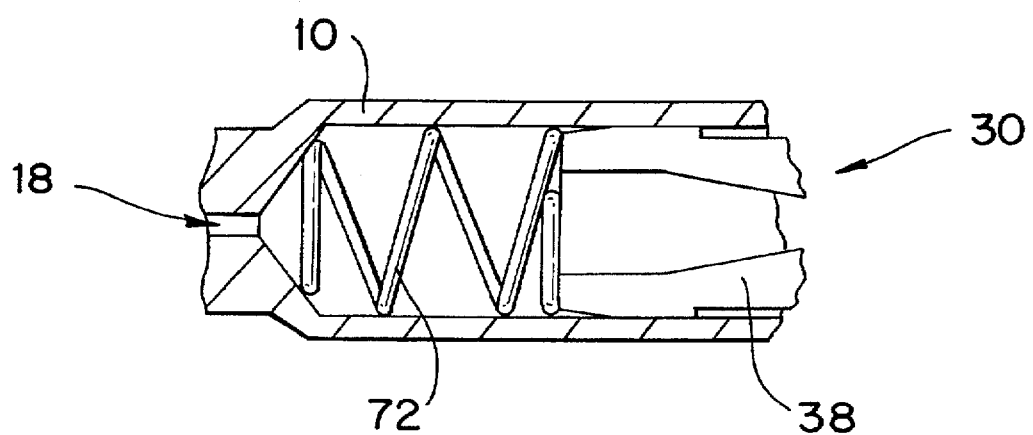
FIG. 5 illustrates a cross-section of a portion of another embodiment of the invention having a rearwardly biased plunger.

In another embodiment, shown in FIG. 5, the plunger 30 is rearwardly biased, preferably by a spring 72 disposed inside the sleeve 10 that presses against a front surface of the plunger 30. A drilling guide of this embodiment automatically extends when pressure on the platform 36 is removed. Thus, if a surgeon has partially drilled a hole, but decides to realign it, the drilling guide will still indicate the current depth of the tool 48 while the surgeon partially or wholly retracts the tool from the bone 56. This feature is especially useful when larger drill bits are used.

In embodiments comprising a sleeve and a plunger, the sleeve need not be at the front of the drilling guide. Further embodiments may place the plunger at the front, to abut the bone, and the sleeve at the rear, to abut the drill. Still further embodiments may have a workpiece-abutment member and a chuck-abutment member with different shapes and mechanisms than those of the sleeves and plungers described.

Also, as stated above, the invention may be tailored to accept other drilling tools including other types of guide wires, Kirschner wires, pins, and drill bits, and the tip 20 may be adapted to abut other types of workpieces such as skin.

What is claimed:

1. A measuring device for measuring penetration depth of a drilling tool being held in a chuck, the device comprising:
- a workpiece-abutment member having a workpiece-abutment end adapted for abutting a workpiece and having a first aperture configured for receiving a protruding portion of the tool that protrudes from the chuck, the protruding portion having a preselected protruding length;
- a chuck-abutment member being collapsibly associated with said workpiece-abutment member and having a chuck-abutting end adapted for abutting the chuck and having a second aperture adapted to axially receive the protruding portion of the tool, said abutment members having a variable combined length that is adjustable up to substantially the protruding length; and
- a frictional member associated with one of said abutment members and biased against another of said abutment members for increasing friction therebetween sufficiently for maintaining the abutment members in a selected collapsed position during withdrawal of the protruding portion of the tool from the abutment members;
- wherein the penetration depth is determinable by a change in the combined length as the tool is drilled into the workpiece axially through the device and as the chuck collapses said abutment members to the collapsed position.

2. The device of claim 1, wherein the frictional member comprises a resilient member associated with one of said abutment members and resiliently biased against another of said abutment members for increasing the friction therebetween sufficiently for maintaining the abutment members in the collapsed position during the withdrawal of the tool.

3. The device of claim 1, wherein said tool is a guide wire.

4. The device of claim 1, further comprising gradations on one of said abutment members being comparable with a part of another of said abutment members for visually determining the change in the combined length.

5. The device of claim 1, further comprising:
- a first stop attached to said workpiece-abutment member; and
- a second stop attached to said chuck-abutment member, said stops interacting for preventing further extension when said abutment members are fully extended.

6. The device of claim 1, further comprising the tool, wherein the tool includes indicia for aligning with a portion of the chuck for setting said preselected protruding length.

7. The device of claim 1, further comprising an alignment member mounted to the workpiece-abutment member and having an alignment bore being adapted to slidably receive a parallel guide-wire such that said first and second apertures align the tool the parallel guide-wire at a predetermined distance therefrom.

8. The device of claim 7, wherein said alignment member forms a handle.

9. The device of claim 1, wherein said workpiece-abutment member has a serrated tip for frictionally engaging the workpiece, said first aperture extending through said tip.

10. The device of claim 1, wherein said abutment members are rotationally fixed to one another.

11. The device of claim 1, wherein said apertures are adapted to guide the tool.

12. The device of claim 1, wherein:
- one of said abutment members comprises a sleeve;
- another of said abutment members comprises a plunger being telescopically slidable within said sleeve; and
- said apertures comprise coaxial bores.

13. A handheld drilling-guide for measuring penetration depth of drilling tool being held in a chuck, the drilling guide comprising:
- a sleeve;
- a plunger being telescopically disposed within said sleeve and having an axial bore adapted to slidably receive and guide a portion of the tool that protrudes from the chuck having a preselected protruding length, and said plunger and said sleeve having a variable combined length being adjustable up to substantially the protruding length; and
- a resilient member attached to one of the plunger and the sleeve and being radially biased by the other of the plunger and the sleeve for increasing friction between said sleeve and said plunger sufficiently for maintaining the abutment members in a selected collapsed position during withdrawal of the protruding portion of the tool from the abutment members;
- wherein the penetration depth is determinable by a change in the combined length when the tool is drilled into a workpiece axially through the guide and the chuck telescopically collapses said plunger into said sleeve to the collapsed position.

14. The device of claim 13, further comprising a handle associated with the sleeve, wherein the handle allows control of the drilling guide by grasping of solely the handle by a user.

15. The drilling guide of claim 13, wherein the resilient member is attached to said plunger, disposed inside the sleeve, and is inwardly biased by the sleeve for increasing the friction between said sleeve and said plunger sufficiently for maintaining the abutment members in the collapsed position during the withdrawal of the tool.

16. The drilling guide of claim 15, wherein said resilient member comprises at least one resilient finger.

17. The drilling guide of claim 13, further comprising:
- an endcap fastened to an end of said sleeve, having an axial endcap-hole for slidably receiving said plunger; and
- a plunger stop attached to said plunger, said plunger stop and said endcap interacting to prevent further extension when said sleeve and said plunger are fully extended.

18. The drilling guide of claim 17, wherein said plunger stop comprises the resilient member, which includes a plurality of fingers extending radially beyond the endcap hole.

19. The drilling guide of claim 13, further comprising:
- an indicator affixed to said sleeve; and
- numbered graduations on a surface of the plunger being visually readable against the indicator for indicating the penetration depth.

20. The drilling guide of claim 13, wherein the plunger and the sleeve have noncircular cross-sections for preventing relative rotation between the plunger and the sleeve.

21. Instrumentation for measuring penetration depth of a drilling tool held in a chuck, the instrumentation comprising:
- a drilling tool having indicia for aligning with a portion of the chuck for preselecting a protruding length of a protruding portion of the tool protruding from said chuck; and
- measuring guide having a workpiece-abutment member and a chuck-abutment member, the workpiece-abutment member having an end adapted for abutting a workpiece and an aperture adapted to axially receive and guide said protruding portion, the chuck-abutment member being collapsibly associated with said workpiece-abutment member and having an end adapted for abutting the chuck and an aperture adapted to axially receive and guide the protruding portion, wherein the guide includes a stop;

wherein said abutment members have a variable combined length, and the stop is associated with the abutment members for limiting extension of the combined length up to substantially the protruding length, the penetration depth being determinable by a change in the combined length as the tool is drilled into the workpiece axially through the device and as the chuck collapses said abutment members.

22. The instrumentation of claim 21, further comprising a depth gage cooperatively associated with the abutment members for indicating the penetration depth by indicating the change in the combined length.

23. The instrumentation of claim 22, wherein the depth gage includes graduations on a surface of one of the abutment members, wherein the graduations are visually readable against the other of the abutment members for directly indicating the penetration depth.

24. A method of measuring the penetration depth of a drilling tool held in a chuck, the method comprising:

securing a drilling tool in a chuck such that a protruding portion of the drilling tool having a preselected protruding length protrudes from the chuck;

inserting said protruding portion into a collapsible drilling guide;

extending the drilling guide to substantially the length of the protruding portion;

placing the drilling guide against a workpiece;

drilling the tool into the workpiece and concurrently collapsing the drilling guide with the chuck; and determining the depth of tool penetration into the workpiece by a change in length of the drilling guide.

* * * * *